(12) United States Patent
Moon

(10) Patent No.: US 9,233,243 B2
(45) Date of Patent: Jan. 12, 2016

(54) LOW FREQUENCY STIMULATOR USING MUSIC AND DIET SYSTEM INCLUDING LOW FREQUENCY STIMULATOR

(71) Applicant: Chan Gon Moon, Seoul (KR)

(72) Inventor: Chan Gon Moon, Seoul (KR)

( * ) Notice: Subject to any disclaimer, the term of this patent is extended or adjusted under 35 U.S.C. 154(b) by 0 days.

(21) Appl. No.: 14/234,398

(22) PCT Filed: Nov. 5, 2012

(86) PCT No.: PCT/KR2012/009252
§ 371 (c)(1),
(2) Date: Jan. 23, 2014

(87) PCT Pub. No.: WO2013/066135
PCT Pub. Date: May 10, 2013

(65) Prior Publication Data
US 2014/0236040 A1    Aug. 21, 2014

(30) Foreign Application Priority Data

Nov. 4, 2011   (KR) .................. 10-2011-0114362
Nov. 2, 2012   (KR) .................. 10-2012-0123726

(51) Int. Cl.
| | |
|---|---|
| *A61N 1/00* | (2006.01) |
| *A61N 1/36* | (2006.01) |
| *A61B 5/053* | (2006.01) |
| *A61B 5/00* | (2006.01) |
| *A61N 1/04* | (2006.01) |

(52) U.S. Cl.
CPC .......... *A61N 1/36014* (2013.01); *A61B 5/0537* (2013.01); *A61B 5/4872* (2013.01); *A61N 1/0484* (2013.01); *A61N 1/0492* (2013.01); *A61N 1/36* (2013.01)

(58) Field of Classification Search
USPC ........................................ 607/115
See application file for complete search history.

(56) References Cited

U.S. PATENT DOCUMENTS

| | | | | |
|---|---|---|---|---|
| 4,813,419 | A * | 3/1989 | McConnell | ............ 607/56 |
| 2008/0033229 | A1 | 2/2008 | Park | |
| 2011/0029044 | A1 | 2/2011 | Hyde | |

FOREIGN PATENT DOCUMENTS

| | | |
|---|---|---|
| EP | 0204525 | 12/1986 |
| JP | 63-95067 | 4/1988 |
| JP | 63-95072 | 4/1988 |
| JP | 2000-060928 | 2/2000 |
| JP | 2001-283502 | 10/2001 |

(Continued)

OTHER PUBLICATIONS

The Office Action and European Search Report, European Patent Office, Jul. 10, 2015, European Patent Application No. 12846080.5.

*Primary Examiner* — Nicole F Lavert
(74) *Attorney, Agent, or Firm* — Lex IP Meister, PLLC

(57) ABSTRACT

The present invention relates to a low-frequency stimulator using music, and a weight-loss assisting system having a low-frequency stimulator. The low-frequency stimulator according to an embodiment of the present invention includes: a beat extracting unit extracting a beat through a sound pressure magnitude comparison between one or more acoustic signals having different frequencies generated when music is played on a music player; a pulse generator generating a pulse having the same magnitude as that of the extracted beat; and a pair of electrode pads attached to a user's body and applying an electrical stimulus having an intensity corresponding to the magnitude of the generated pulse to the user's body.

6 Claims, 8 Drawing Sheets

(56) References Cited

FOREIGN PATENT DOCUMENTS

| | | |
|---|---|---|
| JP | 2002-311953 | 10/2002 |
| JP | 2002-345979 | 12/2002 |
| JP | 2003-000729 | 1/2003 |
| JP | 2007-033851 | 2/2007 |
| KR | 2003-0084396 | 11/2003 |
| KR | 2004-0008746 | 1/2004 |
| KR | 10-2005-0032858 | 4/2005 |
| KR | 2009-0058226 | 6/2009 |
| WO | 2007-148845 | 12/2007 |

* cited by examiner

LOW FREQUENCY STIMULATOR USING MUSIC AND DIET SYSTEM INCLUDING LOW FREQUENCY STIMULATOR

TECHNICAL FIELD

The present invention relates to a low frequency stimulator, and a diet system including the low frequency stimulator, and more particularly, to a technology of extracting a beat from acoustic signals generated by a played music, applying electrical stimulation having an intensity corresponding to a size of the beat to a body of a user through electrode pads, and measuring body fat of the user through the electrical pads.

BACKGROUND ART

A low frequency stimulator, which is a device used for normal blood circulation, relief of acute and chronic pain, fatigue recovery, muscular power increase, and forced exercise of muscle, is a device for achieving a therapy effect or a diet effect by modulating a predetermined power energy to a low frequency pulse, amplifying the low frequency pulse and supplying the amplified low frequency pulse to one pair of conductive electrodes (electrode pads), bringing the pair of electrode pads into contact with a body of a user, and generating electrical stimulation to the body of the user.

The low frequency stimulator includes a low frequency generating device therein in order to generate a low frequency necessary for generating the electrical stimulation, and uses a principle in which when the low frequency stimulator transmits the generated low frequency to one pair of electrode pads, a current flows from one electrode pad to the other electrode pad through the body of the user, and in this process, the electrical stimulation is generated in the body of the user positioned between the one pair of electrode pads.

The low frequency stimulator has been improved so as to generate various types of low frequencies by the low frequency generating device, and has used the various types of low frequencies by periodically and repeatedly generating the various types of low frequencies.

The low frequency stimulator is used for relieving muscular pain after exercise of a shoulder, a waist, a knee, and an ankle, or dieting through muscle strengthening, and has four modes including a tapping mode, a massage mode, a kneading mode, and an automatic mode, a function of adjusting a speed of simulation applied to a muscle, an automatic power saving function, and the like.

However, the low frequency stimulator in the related art uses an LED for displaying an operation mode and the like of the portable low frequency stimulator, so that a user needs to inconveniently recognize an operation mode indicated by a flickering state of the LED through a manual and the like one by one.

Further, the low frequency stimulator in the related art uniformly generates a low frequency according to a program embedded therein, so that when the user first uses the low frequency stimulator, the user may have an interest in the low frequency stimulator, but when the user repeatedly use the low frequency stimulator, the user receives the same low frequency treatment, so that the user disadvantageously loses interest. That is, the low frequency stimulator in the related art generates a low frequency corresponding to a set operation mode, for example, a kneading mode, and repeatedly applies the same stimulation to the muscle of the user until the treatment ends, so that when the user repeatedly uses the low frequency stimulator, the user may become mentally bored.

Further, in a medical aspect, when the user uses the low frequency stimulator in the related art, an effect thereof is good in an initial stage, but when the user frequently uses the low frequency stimulator, the body of the user acquires a tolerance to electrical stimulation of the same low frequency pulse pattern, so that there is a problem in that a therapy effect or a diet effect may deteriorate.

In order to solve the problem, there is suggested a low frequency stimulator applying electrical stimulation to the body of the user by using various pulse patterns, but the various pulse patterns are simply used, and when the user frequently uses the low frequency stimulator having the various pulse patterns, the body of the user also acquires a tolerance to the electrical stimulation by the various pulse patterns, so that there is a problem in that a therapy effect or a diet effect may deteriorate. A prior art document related to the present invention includes Korean Patent No. 10-0475676 (registered on Feb. 28, 2005).

The above information disclosed in this Background section is only for enhancement of understanding of the background of the invention and therefore it may contain information that does not form the prior art that is already known in this country to a person of ordinary skill in the art.

DISCLOSURE

Technical Problem

The present invention has been made in an effort to provide a low frequency stimulator applying electrical stimulation having an intensity corresponding to a size of a beat variously changed in a played music to a body of a user.

The present invention has been made in an effort to provide a diet system of compulsorily exercising a muscle of a user by using a low frequency stimulator applying electrical stimulation having an intensity corresponding to a size of a beat variously changed in a played music to a body of a user through an electrode pad, and measuring body fat of the user through the electrode pad of the low frequency stimulator.

An object to be solved in the present invention is not limited to the aforementioned objects, and other objects not-mentioned herein will be clearly understood by those skilled in the art from descriptions below.

Technical Solution

An exemplary embodiment of the present invention provides a low frequency stimulator, including: a beat extraction unit configured to extract a beat through a comparison of sizes of sound pressures between one or more acoustic signals having different frequencies generated when music is played by a music playing device; a pulse generation unit configured to generate a pulse having the same size as a size of the extracted beat; and one pair of electrode pads attached to a body of a user and configured to apply electrical stimulation having an intensity corresponding to a size of the generated pulse to the body of the user.

The beat extraction unit may include: a band mode selection unit configured to receive selection of any one between a single register band mode and a plural-register band mode from the user; a single register band beat extraction unit configured to extract an acoustic signal having a frequency of a single register band in which a sound pressure size is largest through a comparison of sizes of sound pressures of some or all of the acoustic signals having the frequency of the single register band among the one or more acoustic signals as the beat for each unit time according to the selection of the single register band mode; and a plural-register band beat extraction unit configured to extract an acoustic signal having a frequency belonging to a plural-register band in which a sound pressure size is largest through a comparison of sizes of sound pressures of some or all of the acoustic signals having the frequency belonging to the plural-register bands among the one or more acoustic signals as the beat for each unit time according to the selection of the plural-register band mode.

The single register band beat extraction unit may include: a single band pass filter configured to allow some or all of the acoustic signals having the frequency of the single register band among the one or more acoustic signals to pass through for each unit time; a single register analog/digital conversion unit configured to digital-convert some of all of the acoustic signals having the frequency of the single register band; and a single register extraction unit configured to extract an acoustic signal having the largest sound pressure size among some or all of the digital-converted acoustic signals as the beat.

The single register band may be a band in which a frequency is 20 to 200 Hz.

The plural-register band beat extraction unit may include: a first band pass filter configured to allow some or all of the acoustic signals having a frequency of a first register band among one or more acoustic signals to pass through; a second band pass filter configured to allow some or all of the acoustic signals having a frequency of a second register band among one or more acoustic signals to pass through; a third band pass filter configured to allow some or all of the acoustic signals having a frequency of a third register band among one or more acoustic signals to pass through; a plural-band analog/digital conversion unit configured to digital-convert some or all of the acoustic signals having the frequency of the first register band, some or all of the acoustic signals having the frequency of the second register band, and some or all of the acoustic signals having the frequency of the third register band; and a plural-band extraction unit configured to extract the acoustic signal having the largest sound pressure size from the digital-converted some or all of the acoustic signals having the frequency of the first register band, some or all of the acoustic signals having the frequency of the second register band, and some or all of the acoustic signals having the frequency of the third register band as the beat.

The first register band may be a band in which a frequency is 20 to 100 Hz, the second register band may be a band in which a frequency is 101 to 200 Hz, and the third register band may be a band in which a frequency is 201 to 700 Hz.

The unit time may be 0.05 to 0.1 second.

Another exemplary embodiment of the present invention provides a diet system, including: the low frequency stimulator; and a body fat measuring unit configured to calculate body fat of a user by using body impedance of the user measured through one pair of electrode pads of the low frequency stimulator.

Advantageous Effects

According to the exemplary embodiment of the present inventions, electrical stimulation having an intensity corresponding to a size of a beat variously varying in played music is applied to a body of a user, so that the user may feel vibration having a size corresponding to the variously varying beat according to a flow of time, thereby receiving a treatment without being bored until the treatment ends.

Further, electrical stimulation having an intensity corresponding to a size of a beat variously varying in played music is applied to a body of a user, so that it is possible to prevent a therapy effect or a diet effect from deteriorating due to a tolerance to the same electrical stimulation generated to the body of the user when electrical stimulation by the same low frequency pulse pattern is repeatedly applied to a body of a user.

Further, a muscle of a user may be compulsorily exercised by using the low frequency stimulator, which applies electrical stimulation having an intensity corresponding to a size of a beat variously varying in a played music to the body of the user through the electrode pads and then body fat of the user may be measured through the electrode pads of the low frequency stimulator, thereby measuring body fat before and after muscle exercise without a separate body fat measuring device.

MODE FOR INVENTION

Hereinafter, an exemplary embodiment of the present invention will be described in detail with reference to the accompanying drawings. In the following description of the exemplary embodiment of the present invention, a detailed description of known functions and configurations incorporated herein is omitted to avoid making the subject matter of the present invention unclear. In addition, the terminology used in the description is defined in consideration of the function of corresponding components used in the present invention may be varied according to users, operator's intention, or practices. Therefore, the definitions should be made based on the entire contents of the present specification.

Figure 1:
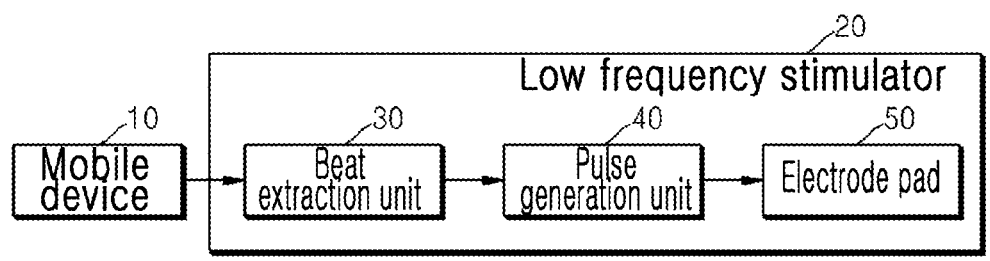
FIG. 1 is a diagram illustrating a configuration of a low frequency stimulator according to an exemplary embodiment of the present invention.
Figure 2:
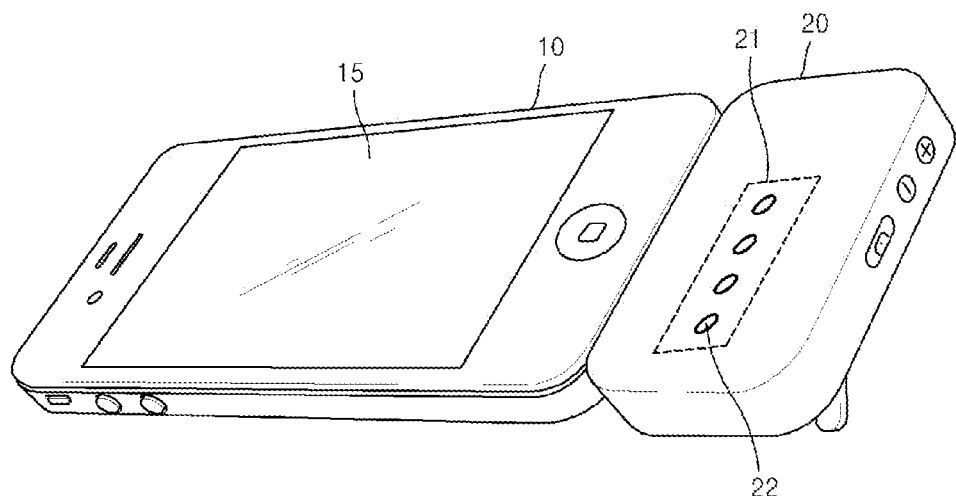
FIG. 2 is a perspective view illustrating a connection between the low frequency stimulator of FIG. 1 and a mobile device.

FIG. 1 is a block diagram illustrating a configuration of a low frequency stimulator according to an exemplary embodiment of the present invention, and FIG. 2 is a perspective view illustrating an example of a connection relationship between the low frequency stimulator of FIG. 1 and a mobile device. Referring to FIGS. 1 and 2, a low frequency stimulator 20 according to the present invention includes a beat extraction unit 30, a pulse generation unit 40, and electrode pads 50.

The beat extraction unit 30 extracts a beat through a comparison of sizes of sound pressures of one or more acoustic signals having different frequencies generated during a play of music by a music playing device.

In this case, the music playing device may be a mobile device 10, or a music playing device (not illustrated) included inside the low frequency stimulator 20. Accordingly, a sound source of music may be stored in the mobile device 10 or stored in the low frequency stimulator 20.

In order to provide acoustic signals of the music played by the mobile device 10 to the beat extraction unit 30 of the low frequency stimulator 20, an interface needs to be included between the mobile device 10 and the low frequency stimulator 20. The interface serves to provide the acoustic signals of the music played by the mobile device 10 to the low frequency stimulator 20. In this case, the mobile device 10 may be a smart phone, a mobile phone, a notebook computer, a PMP, an MP3 player, and the like.

As the exemplary embodiment, in a case where the mobile device 10 is an Android phone, the acoustic signals generated by the music played by the mobile device 10 may be provided to the beat extraction unit 30 of the low frequency stimulator 20 through an earphone cable connected to an earphone terminal of the mobile device 10 or a Bluetooth module of the mobile device 10. In correspondence with this, the beat extraction unit 30 may include an earphone terminal for a connection with the earphone cable connected to the mobile device 10, or a Bluetooth module. The earphone terminal or the Bluetooth module may be separately included inside the low frequency stimulator 20, not the beat extraction unit 30.

In the meantime, in a case where the mobile device 10 is the iPhone of the Apple Inc., the acoustic signals generated by the music played by the mobile device 10 may be provided to the beat extraction unit 30 of the low frequency stimulator 20 through a connector fastened to a connector pin of the mobile device 10 or a Bluetooth module of the mobile device 10. In correspondence with this, the beat extraction unit 30 may include a connector terminal to which a 30-pin connector connected to the mobile device 10 is fastened, or a Bluetooth module. The connector terminal or the Bluetooth module may be separately included inside the low frequency stimulator 20, not the beat extraction unit 30.

The low frequency stimulator 20 may be a portable type portable by a user or a fixed type fixed and used at a place, such as a hospital. When the low frequency stimulator 20 is the portable type, operation power of the low frequency stimulator 20 may be provided from a battery included inside the low frequency stimulator 20 or provided from the mobile device 10. In this case, in a case where the mobile device 10 is the Android phone, the operation power may be supplied to the low frequency stimulator 20 through a USB cable fastened to a USB terminal of the mobile device 10. In correspondence with this, the low frequency stimulator 20 needs to include a USB terminal for receiving the operation power provided from the mobile device 10. In the meantime, when the mobile device 10 is the iPhone, the operation power may be supplied to the low frequency stimulator 20 through the connector fastened to the connector pin of the mobile device 10. In correspondence with this, the low frequency stimulator 20 needs to include a connector terminal for receiving the operation power provided from the mobile device 10.

As described above, the low frequency stimulator 20 may include all of the interfaces (the earphone terminal, the USB terminal, the Bluetooth module, and the connector terminal) changed depending on the types of mobile device 10, or include only an interface connected with one type of the mobile device, for example, the earphone terminal or the Bluetooth module for receiving an acoustic signal and the USB terminal for supplying the operation power in a case where the mobile device 10 is the Android phone, and the connector terminal in a case where the mobile device 10 is the iPhone.

In general, music includes various factors, such as rhythm, a melody, a tempo, time, and a beat, which will be simply described.

Rhythm, expressed in a manner such as "Ddan Ddada", represents an expression of various feelings by adjusting a length of a note.

Melody represents a pattern made by using a difference in a tune and a rhythm, such as "sol, ra, ra, sol, sol, mi, sol, sol, mi, mi, re".

Tempo represents a speed of music.

Time will be described below. For example, four-four time means that 4 quarter notes are included in one measure, and six-eight time means that 6 eighth notes are included in one measure.

Beat is used as the same meaning as that of the time, but generally represents the number of notes into which one measure is split. For example, the split of one measure into 8 eighth notes in music in four-four time is referred to as 8 beats, and the split of one measure into 16 sixteenth notes is referred to as 16 beats. That is, the beat represents a strong beat in a basic time, and a musical instrument giving a beat includes a base drum, a base guitar, and other low-pitched tone musical instrument.

This will be further described based on a waltz in three-four time. The rhythm is like "lalarla lalarla", the time is like "Ggungjakjak Ggungjakjak", and the beat is like "Ggung . . . . Ggung . . . . ".

As described above, the low frequency stimulator 20 according to the exemplary embodiment of the present invention extracts a factor of the music, that is, the beat, and converts the extracted factor into a low frequency pulse, and then applies the electrical stimulation to the body of the user, so that in a case where the user uses various music, the user may receive a treatment while receiving electrical stimulation varying in real time, so that the user may not be bored until the treatment ends.

Figure 3:
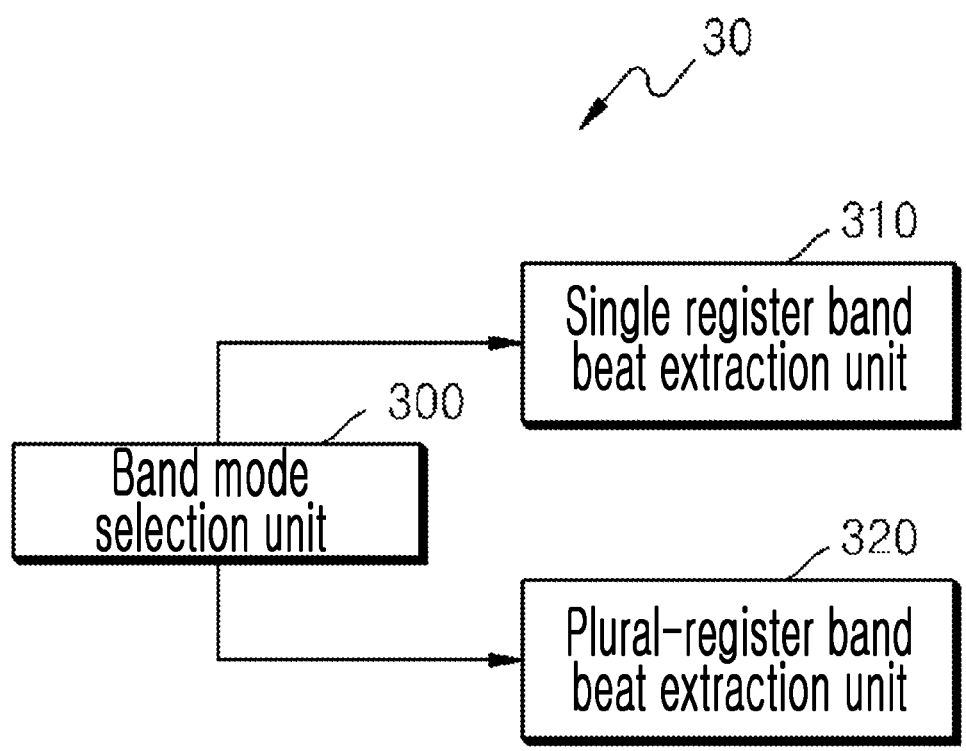
FIG. 3 is a diagram illustrating a detailed configuration of a beat extraction unit of FIG. 1.

A detailed configuration of the beat extraction unit 30 is illustrated in FIG. 3. Referring to FIG. 3, the beat extraction unit 30 includes a band mode selection unit 300, a single register band beat extraction unit 310, and a plural-register band beat extraction unit 320.

The band mode selection unit 300 receives selection of any one between a single register band mode and a plural-register band mode from the user. The band mode selection unit 30 includes a single register band mode key (not illustrated) and a plural-register band mode key (not illustrated) in the low frequency stimulator 20, and the user may select the single register band mode or the plural-register band mode through selection of each key. This simply corresponds to an exemplary embodiment, and the present invention is not limited thereto.

When the user selects the single register band mode through the band mode selection unit 300, the single register band beat extraction unit 310 extracts an acoustic signal having a frequency of the single register band in which a sound pressure size is largest as the beat through a comparison of sizes of the sound pressures between some or all of the acoustic signals having the frequency of the single register band among one or more acoustic signals for each unit time.

Figure 4:
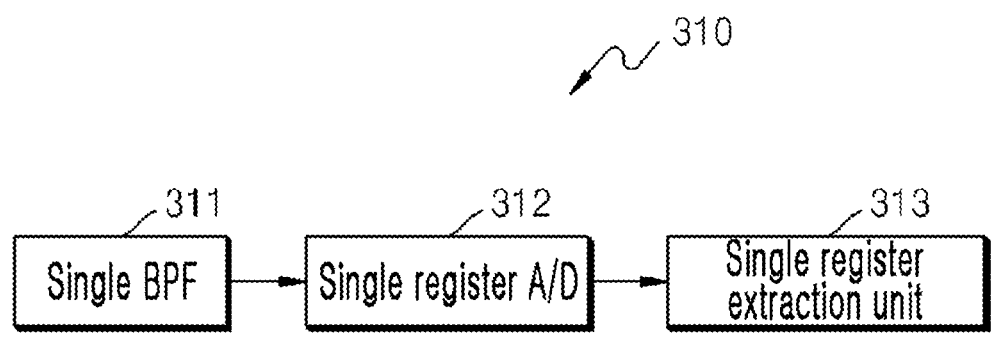
FIG. 4 is a diagram illustrating a configuration of a single register band beat extraction unit of FIG. 3.

The single register band beat extraction unit 310 includes a single band pass filter 311, a single register analog/digital conversion unit 312, and a single register extraction unit 313 as illustrated in FIG. 4.

The single band pass filter 311 allows some of all of the acoustic signals having the frequency of the single register band among one or more acoustic signals for each unit time to pass through.

The single register analog/digital conversion unit 312 digital converts some or all of the acoustic signals having the frequency of the single register band.

The single register extraction unit 313 extracts an acoustic signal having the largest sound pressure size among some or all of the acoustic signals digital-converted by the single register analog/digital conversion unit 312 as the beat.

In this case, the single register band may be a band in which a frequency is 20 to 200 Hz, but is not limited thereto and may be changed according to selection by the user. The frequency range of the single register band may be changed by various methods, as well as selection by the user. Further, the unit time may be 0.05 to 0.1 second, but a range of the unit time is not limited thereto, and may be changed according to selection by the user. The range of the unit time may be changed by various methods, as well as selection by the user.

Referring back to FIG. 3, when the user selects the plural-register band mode through the band mode selection unit 300, the plural-register band beat extraction unit 320 extracts an acoustic signal having a frequency belonging to the plural-register band in which the sound pressure size is largest as the beat through a comparison of sizes of sound pressures between some or all of the acoustic signals having a frequency belonging to the plural register bands among the one or more acoustic signals for each unit time.

Figure 5:
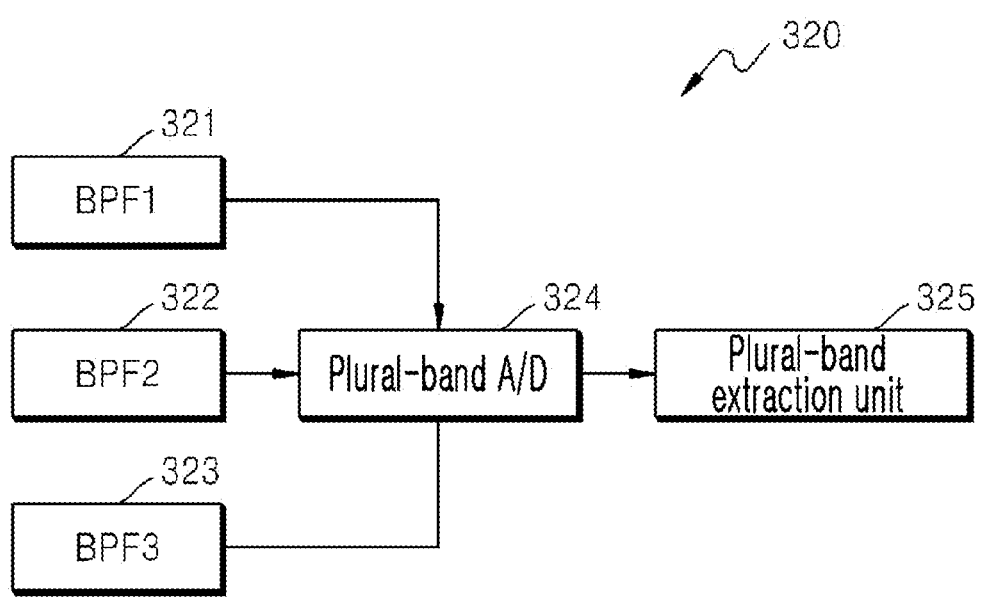
FIG. 5 is a diagram illustrating a configuration of a plural-register band beat extraction unit of FIG. 3.

The exemplary embodiment for the configuration of the plural-register band beat extraction unit 320 is illustrated in FIG. 5. Referring to FIG. 5, the plural-register band beat extraction unit 320 includes a first band pass filter 321, a second band pass filter 322, a third band pass filter 323, a plural-band analog/digital conversion unit 324, and a plural-band extraction unit 325.

The first band pass filter 321 allows some or all of the acoustic signals having a frequency of a first register band among the one or more acoustic signals to pass through. In this case, the first register band may be a band in which a frequency is 20 to 100 Hz, but is not limited thereto and may be changed according to selection by the user. Further, a frequency range of the first register band may be changed by various methods, as well as selection by the user.

The second band pass filter 322 allows some or all of the acoustic signals having a frequency of a second register band among the one or more acoustic signals to pass through. In this case, the second register band may be a band in which a frequency is 101 to 200 Hz, but is not limited thereto and may be changed according to selection by the user. Further, a frequency range of the second register band may be changed by various methods, as well as selection by the user.

The third band pass filter 323 allows some or all of the acoustic signals having a frequency of a third register band among the one or more acoustic signals to pass through. In this case, the third register band may be a band in which a frequency is 201 to 700 Hz, but is not limited thereto and may be changed according to selection by the user. Further, a frequency range of the third register band may be changed by various methods, as well as selection by the user.

The plural-band analog/digital conversion unit 324 digital converts some or all of the acoustic signals having the frequency of the first register band, some or all of the acoustic signals having the frequency of the second register band, and some or all of the acoustic signals having the frequency of the third register band.

The plural-band extraction unit 325 extracts the acoustic signal having the largest sound pressure size among some or all of the acoustic signals having the frequency of the first register band, some or all of the acoustic signals having the frequency of the second register band, and some or all of the acoustic signals having the frequency of the third register band digital converted by the plural-band analog/digital conversion unit 324 as the beat.

The plural-band extraction unit 325 extracts the acoustic signal having the largest sound pressure size among the acoustic signals having different frequencies of the plural bands as the beat for each unit time. Accordingly, the plural-band extraction unit 325 may extract the beat through the comparison of the sizes of the sound pressures even when only one acoustic signal generated by the music played in the music playing device enters or the plurality of acoustic signals enters for the unit time.

Referring back to FIG. 1, the pulse generation unit 40 generates a pulse having the same size as that of the beat extracted by the beat extraction unit 30 and applies the generated pulse to the electrode pads 50.

A pair of electrode pads 50 is attached to the body of the user, and applies electrical stimulation having an intensity corresponding to a size of the pulse applied by the pulse generation unit 40 to the body of the user. In this case, when the single register band beat extraction unit 310 of FIG. 3 extracts the acoustic signal having a band frequency from 20 to 200 Hz as the beat, converts the extracted beat to a pulse, and then applies the converted pulse to the body of the user through one pair of electrode pads, an effect that the user receives stimulation of "tapping" is achieved. In the meantime, when the plural-register band beat extraction unit 320 of FIG. 3 extracts the acoustic signal having a band frequency from 20 to 100 Hz as the beat, converts the extracted beat to a pulse, and then applies the converted pulse to the body of the user through one pair of electrode pads, an effect that the user receives stimulation of "tapping" is achieved. When the plural-register band beat extraction unit 320 extracts the acoustic signal having a band frequency from 101 to 200 Hz as the beat, converts the extracted beat to a pulse, and then applies the converted pulse to the body of the user through one pair of electrode pads, an effect that the user receives stimulation of "kneading" is achieved. When the plural-register band beat extraction unit 320 extracts the acoustic signal having a band frequency from 201 to 700 Hz as the beat, converts the extracted beat to a pulse, and then applies the converted pulse to the body of the user through one pair of electrode pads, an effect that the user receives stimulation of "pressing" is achieved.

The low frequency stimulator in the related art generates a low frequency and repeatedly gives the same stimulation to a muscle of a user until a treatment ends, so that the user may be bored when repeatedly using the low frequency stimulator. However, the low frequency stimulator according to the exemplary embodiment of the present invention extracts beats from acoustic signals of various music generates a low frequency pulse corresponding to a size of the extracted beat, and applies electrical stimulation of the body to the user through the electrode pads, so that the user feels vibration having a size corresponding to the beat variously varying according to a time, and receives a treatment without being bored until the treatment ends.

The configuration of the low frequency stimulator 20 according to the exemplary embodiment of the present invention relates to automatically extracting beats from acoustic signals of played music, generating a low frequency pulse corresponding to a size of the extracted beat, and electrically stimulating a body of a user through one pair of electrode pads. In addition, the low frequency pulse applied to the one pair of electrode pads maybe generated according to information manually input by the user. To this end, the low frequency stimulator 20 may further include a low frequency pulse selection unit (not illustrated) for selecting the type of low frequency pulse applied to the electrode pad, a size adjustment means (not illustrated) for adjusting a size of the low frequency pulse, and a low frequency generation unit (not illustrated) for generating the low frequency pulse selected by the low frequency pulse selection unit to have the size adjusted by the size adjustment means and applying the generated low frequency pulse to one pair of electrode pads. Accordingly, the user may receive a low frequency treatment according to an automatically or directly and manually set condition while playing the music.

Further, the low frequency stimulator 20 may include a display unit 21 for displaying a size of the low frequency pulse, and the display unit 21 may be formed of a plurality of LEDs 22. Accordingly, the user may recognize a size of the low frequency pulse applied to the electrode pads while receiving the low frequency treatment. As another exemplary embodiment, the size of the low frequency pulse applied to one pair of electrode pads may be output through a screen 15 of the mobile device 10. To this end, when the low frequency stimulator 20 transmits information about the size of the low frequency pulse to the mobile device 10, the mobile device 10 may output the information about the size of the low frequency pulse received from the low frequency stimulator 20 on the screen 15.

Figure 6:
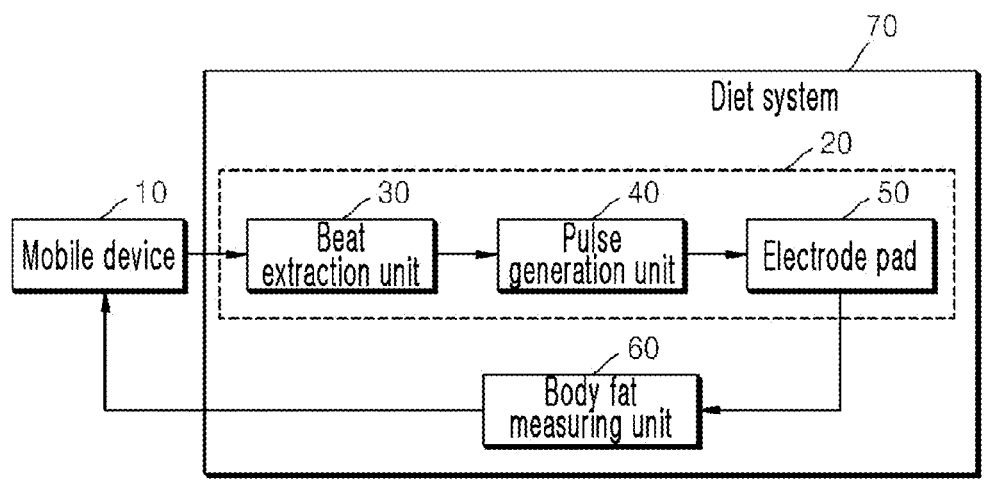
FIG. 6 is a diagram illustrating a configuration of a diet system according to an exemplary embodiment of the present invention.
Figure 7:
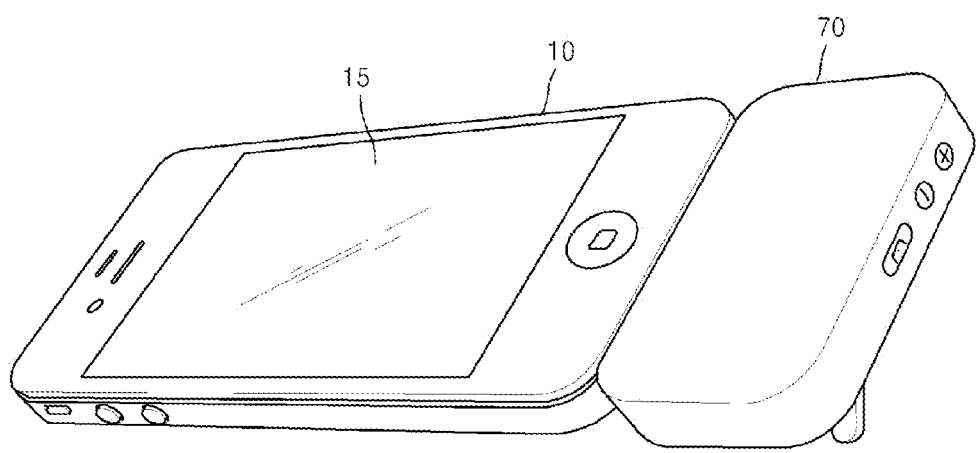
FIG. 7 is a perspective view illustrating an example of a connection relationship between the diet system of FIG. 6 and the mobile device.

FIG. 6 is a diagram illustrating a configuration of a diet system according to an exemplary embodiment of the present invention, and FIG. 7 is a perspective view illustrating an example of a connection relationship between the diet system of FIG. 6 and the mobile device.

Referring to FIGS. 6 and 7, a diet system 70 according to an exemplary embodiment of the present invention includes a low frequency stimulator 20 and a body fat measuring unit 60. In this case, the body fat measuring unit 60 is electrically connected with the electrode pads 50 within the low frequency stimulator 20. Further, referring to FIG. 2, the low frequency stimulator 20 is manufactured in a form having a separate case, but when the low frequency stimulator 20 is included in the diet system 70, the low frequency stimulator 20 may be implemented as a printed circuit board and installed inside the diet system 70. That is, the diet system 70 may include all of the configurations within the aforementioned low frequency stimulator 20.

Further, although not illustrated in the drawing, the diet system 70 may further include a selection unit (not illustrated) allowing the user to select a low frequency stimulation mode and a body fat measuring mode. That is, the user may select the low frequency stimulation mode and the body fat measuring mode through the selection unit. The selection unit may be included in the diet system 70, but may be included in the mobile device 10 as a matter of course.

When acoustic signals of music played by the music playing device are input in a state where the low frequency stimulation mode is selected by the selection unit, the low frequency stimulator 20 extracts a beat through a comparison of sizes of sound pressures of the acoustic signals for each unit time and generates a pulse corresponding to a size of the beat, and then applies electrical stimulation to the body of the user through one pair of electrode pads 50, and may include the beat extraction unit 30, the pulse generation unit 40, and the electrode pads 50. The configuration has been described, so that a description thereof will be omitted.

Figure 8:
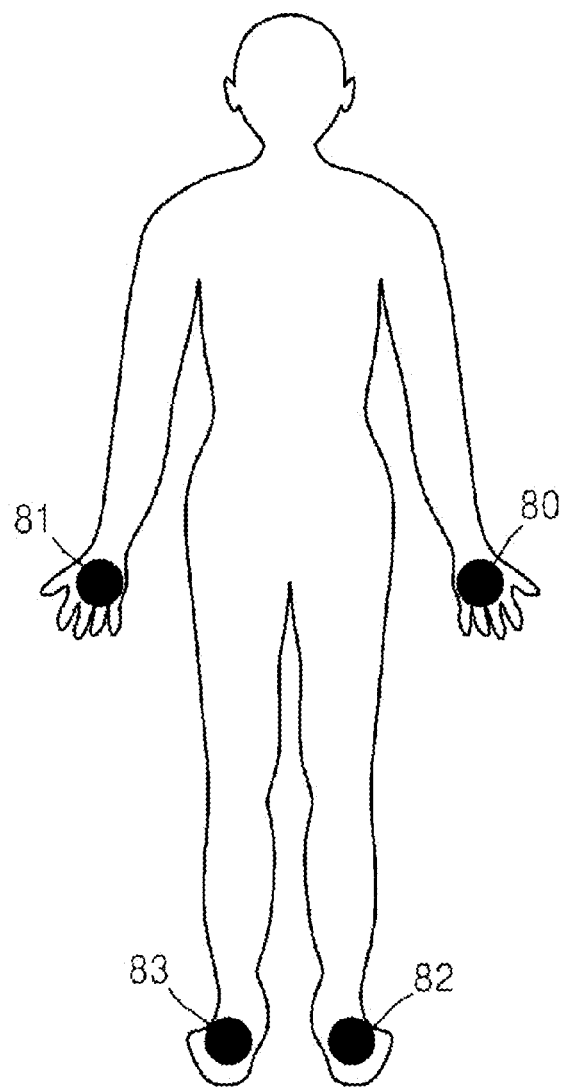
FIG. 8 is a diagram illustrating an example of a body part to which one pair of electrode pads of the low frequency stimulator is attached.

When the body fat measuring mode is selected by the selection unit, the body fat measuring unit 60 calculates body fat of the user by using body impedance of the user measured through one pair of electrode pads 50 of the low frequency stimulator 20. Hereinafter, the calculation of the body fat of the user by using the measured body impedance of the user will be briefly described. The body fat may be measured based on a scheme of the 5-cylinder model. First, as illustrated in FIG. 8, the body fat measuring unit 60 applies a weak current to the body of the user through one pair of electrode pads 50 attached to each of body parts, for example, both hands 80 and 81, and both feet 82 and 83, by the scheme of the 5-cylinder model. Accordingly, electricity flows along water (body water) having high conductivity in the body of the user. When there is a large amount of water inside the body of the user, a path through which electricity flows is widened, and when there is a small amount of water inside the body of the user, a path through which electricity flow is narrowed. This is represented by a measurement value of body resistance, that is, body impedance. Accordingly, the body fat measuring unit 60 may measure the body impedance of the user through the electrode pads 50 of the low frequency stimulator 20 attached to both hands 80 and 81, and both feet 82 and 83. That is, the body fat measuring unit 60 may calculate the body impedance of the user by calculating body impedance between both hands 80 and 81, when viewing the drawing, body impedance between the right hand 81 and a right foot 83, body impedance between the right hand 81 and a left foot 82, body impedance between the left hand 80 and the left foot 82, body impedance between the left hand 80 and the right foot 83, and body impedance between the right foot 83 and the left foot 82 and adding all of the calculated body impedance.

Then, the body fat measuring unit 60 calculates the amount of body water by multiplying a value obtained by dividing a square of height of the user by the body impedance of the user by a constant, and estimates the amount of protein and the amount of minerals of the user by using the amount of body water. A ratio of the amounts of water, protein, minerals, and body fat in the body of a person is 55:20:20:5. Accordingly, after the amount of body water is calculated, the amount of protein of the user is calculated according to the proportional relation and then the amount of minerals is calculated again. Then, when all of the amount of water, the amount of protein, and the amount of minerals are subtracted from whole weight of the user, the amount of body fat, that is, information about the body fat, may be calculated.

The body fat measuring unit 60 may output the calculated information about the body fat to the user through the screen 15 of the mobile device 10. As another exemplary embodiment, the diet system 70 may include a display device (not illustrated) to output the information about the body fat on the screen of the display device.

Accordingly, the user directly massages a muscle through low frequency electrical stimulation weak to the body of the user, calms user's nerves, and facilitates blood circulation through the diet system 70, so that it is helpful in relieving acute and chronic pain by muscle pain. Further, a fat cell and a hyper-nutritive muscle cell (which is a basic unit forming muscle, and is formed of several myofibril) of the body are muscle-massaged and exercised to a fat layer through a beat of rhythmical music through the low frequency electrical stimulation, so that it is possible to dissolve a fat cell in a desired region. Further, it is possible to conveniently measure body fat before and after muscle exercise through the low frequency electrical stimulation through one pair of electrode pads (conductive pads) attached to the body.

The present invention has been described with reference to the exemplary embodiments. Those skilled in the art will appreciate that various modifications are possible without departing from the essential characteristic of the present invention. Accordingly, the disclosed exemplary embodiments need to be considered in an illustrative aspect, not a limiting aspect. Therefore, it shall be construed in such a manner that the scope of the present invention is not limited to the aforementioned exemplary embodiment, and includes the contents described in the accompanying claims and various implementations within the scope equivalent to the claims.

INDUSTRIAL APPLICABILITY

The present invention is applicable to a development field of a medical device.

The invention claimed is:

1. A low frequency stimulator, comprising:
a beat extraction unit configured to extract a beat through a comparison of sizes of sound pressures between one or more acoustic signals having different frequencies generated when music is played by a music playing device;
a pulse generation unit configured to generate a pulse having the same size as a size of the extracted beat; and
one pair of electrode pads configured to a body of a user and configured to apply electrical stimulation having an intensity corresponding to a size of the generated pulse to the body of the user,
wherein the beat extraction unit includes:
a band mode selection unit configured to receive selection of any one between a single register band mode and a plural-register band mode from the user;
a single register band beat extraction unit configured to extract an acoustic signal having a frequency of a single register band in which a sound pressure size is largest through a comparison of sizes of sound pressures of some or all of the acoustic signals having the frequency of the single register band among the one or more acoustic signals as the beat for each unit time according to the selection of the single register band mode; and
a plural-register band beat extraction unit configured to extract an acoustic signal having a frequency belonging to a plural-register band in which a sound pressure size is largest through a comparison of sizes of sound pressures of some or all of the acoustic signals having the frequency belonging to the plural-register bands among the one or more acoustic signals as the beat for each unit time according to the selection of the plural-register band mode.

2. The low frequency stimulator of claim 1, wherein: the single register band beat extraction unit includes: a single band pass filter configured to allow some or all of the acoustic signals having the frequency of the single register band among the one or more acoustic signals to pass through for each unit time; a single register analog/digital conversion unit configured to digital-convert some of all of the acoustic signals having the frequency of the single register band; and a single register extraction unit configured to extract an acoustic signal having the largest sound pressure size among some or all of the digital-converted acoustic signals as the beat.

3. The low frequency stimulator of claim 2, wherein:
the single register band is a band in which a frequency is 20 to 200 Hz.

4. The low frequency stimulator of claim 1, wherein: the plural-register band beat extraction unit includes: a first band pass filter configured to allow some or all of the acoustic signals having a frequency of a first register band among one or more acoustic signals to pass through; a second band pass filter configured to allow some or all of the acoustic signals having a frequency of a second register band among one or more acoustic signals to pass through; a third band pass filter configured to allow some or all of the acoustic signals having a frequency of a third register band among one or more acoustic signals to pass through; a plural-band analog/digital conversion unit configured to digital-convert some or all of the acoustic signals having the frequency of the first register band, some or all of the acoustic signals having the frequency of the second register band, and some or all of the acoustic signals having the frequency of the third register band; and a plural-band extraction unit configured to extract the acoustic signal having the largest sound pressure size from the digital-converted some or all of the acoustic signals having the frequency of the first register band, some or all of the acoustic signals having the frequency of the second register band, and some or all of the acoustic signals having the frequency of the third register band as the beat.

5. The low frequency stimulator of claim 4, wherein:
the first register band is a band in which a frequency is 20 to 100 Hz, the second register band is a band in which a frequency is 101 to 200 Hz, and the third register band is a band in which a frequency is 201 to 700 Hz.

6. The low frequency stimulator of claim 1, wherein: the unit time is 0.05 to 0.1 second.

* * * * *